United States Patent
Hofmann

(10) Patent No.: US 7,757,560 B2
(45) Date of Patent: Jul. 20, 2010

(54) METHODS AND APPARATUS FOR OBSERVING VESSEL CONTENTS

(75) Inventor: Martin John Hofmann, Stroud (GB)

(73) Assignee: Pall Corporation, Port Washington, NY (US)

( * ) Notice: Subject to any disclaimer, the term of this patent is extended or adjusted under 35 U.S.C. 154(b) by 387 days.

(21) Appl. No.: 11/721,364

(22) PCT Filed: Dec. 30, 2005

(86) PCT No.: PCT/EP2005/014153

§ 371 (c)(1),
(2), (4) Date: Jun. 11, 2007

(87) PCT Pub. No.: WO2006/069797

PCT Pub. Date: Jul. 6, 2006

(65) Prior Publication Data

US 2009/0277272 A1 Nov. 12, 2009

(30) Foreign Application Priority Data

Dec. 31, 2004 (GB) ................... 0428547.4

(51) Int. Cl.
*G01R 33/20* (2006.01)
(52) U.S. Cl. ........................ 73/632; 73/290 V
(58) Field of Classification Search .................. 73/632, 73/290 V, 290 R
See application file for complete search history.

(56) References Cited

U.S. PATENT DOCUMENTS

| | | | |
|---|---|---|---|
| 3,520,186 A * | 7/1970 | Adams et al. ............. 73/290 R |
| 4,014,650 A | 3/1977 | Sigelmann | |
| 4,320,659 A * | 3/1982 | Lynnworth et al. ............ 73/589 |
| 4,324,131 A | 4/1982 | Rosencwaig | |
| 4,959,228 A | 9/1990 | Skrgatic et al. | |
| 5,438,868 A * | 8/1995 | Holden et al. ............. 73/290 V |
| 5,473,934 A | 12/1995 | Cobb | |
| 5,533,402 A | 7/1996 | Sarvazyan et al. | |
| 5,708,191 A | 1/1998 | Greenwood et al. | |
| 5,760,309 A * | 6/1998 | Maltby et al. .................. 73/646 |
| 5,831,150 A | 11/1998 | Sowerby et al. | |
| 5,886,250 A | 3/1999 | Greenwood et al. | |

(Continued)

FOREIGN PATENT DOCUMENTS

DE 38 19 540 12/1989

(Continued)

OTHER PUBLICATIONS

Martin Hofmann, *Journal of Chromatography A*, 989:79-94 (2003).

(Continued)

*Primary Examiner*—Hezron Williams
*Assistant Examiner*—Rodney T Frank
(74) *Attorney, Agent, or Firm*—Leydig, Voit & Mayer, Ltd.

(57) ABSTRACT

A method for observing a change in one or more parameters of a flowable material in a vessel is disclosed, the method comprising transmitting an ultrasound signal into a vessel containing a flowable material; observing a change in the ultrasound signal after it has passed through the flowable material; and, relating the change in the ultrasound signal to the change in one or more parameters of the flowable material.

10 Claims, 6 Drawing Sheets

U.S. PATENT DOCUMENTS

| | | | |
|---|---|---|---|
| 6,082,180 | A | 7/2000 | Greenwood |
| 6,082,181 | A | 7/2000 | Greenwood |
| 6,109,097 | A | 8/2000 | Conrads et al. |
| 6,539,794 | B1 * | 4/2003 | Otto et al. ............... 73/290 V |
| 6,763,698 | B2 | 7/2004 | Greenwood |
| 6,843,124 | B2 * | 1/2005 | Otto et al. ............... 73/290 V |
| 6,877,375 | B2 | 4/2005 | Greenwood |
| 7,243,539 | B2 * | 7/2007 | Otto et al. ............... 73/290 V |
| 7,435,284 | B2 | 10/2008 | Piccinini et al. |
| 2003/0051558 | A1 | 3/2003 | Melnikov et al. |
| 2004/0087860 | A1 | 5/2004 | Lee et al. |
| 2004/0090625 | A1 * | 5/2004 | Fischer et al. ............... 356/336 |
| 2004/0139729 | A1 | 7/2004 | Taylor, III et al. |
| 2007/0107594 | A1 | 5/2007 | Piccinini et al. |
| 2009/0272190 | A1 | 11/2009 | Hofmann |

FOREIGN PATENT DOCUMENTS

| | | |
|---|---|---|
| DE | 38 25 131 | 1/1990 |
| DE | 44 37 684 | 4/1996 |
| GB | 2 130 368 | 5/1984 |
| WO | WO 02/50511 | 6/2002 |
| WO | WO 02/071050 | 9/2002 |
| WO | WO 2004/020112 | 3/2004 |
| WO | WO 2004/036150 | 4/2004 |

OTHER PUBLICATIONS

International Preliminary Report on Patentability for PCT/EP2005/014153 mailed Jul. 12, 2007.

Greenwood, M. S., et al., *Journal of Fluids Engineering*, 126(2):189-192 (2004).

* cited by examiner

METHODS AND APPARATUS FOR OBSERVING VESSEL CONTENTS

BACKGROUND OF THE INVENTION

The present invention relates to methods and apparatus for observing flowable material, e.g., observing a change in one in one or more parameters in a flowable material in a vessel, using ultrasound, and particularly relates to monitoring one or more parameters in the flowable material in a vessel using ultrasound, e.g., to determine the presence and/or formation of agglomerates in the flowable material and/or to monitor fermentation.

Observation of changes in the properties of a flowable material in a vessel or monitoring of a process occurring within a vessel are important in a large number of industries. Examples include measurement of changes of the properties of a flowable mixture in a fermentation tank, or monitoring of the progress of a reaction in a pharmaceutical synthesis vessel.

Properties of the flowable materials in vessels have been monitored by using fixed mechanical sensors inside the vessel which measure individual parameters. Alternatively, ultraviolet (UV) spectral measuring equipment may be arranged on the outside of the vessel with a window in the wall of the vessel through which measurements can be made. In either of these cases, specially designed or adapted vessels are required to accept sensor units inside them or with windows or apertures in their walls through which measurements can be made.

It is also known to measure the level of a liquid in a vessel by putting an ultrasound sensor facing down towards the top surface of the liquid and measuring the time of flight (correcting for temperature) of an ultrasound pulse returning after contacting the surface of the liquid.

However, these approaches have suffered from a number of drawbacks, e.g., some are not applicable to certain classes of flowable material, and same provide inaccurate and/or delayed results, requiring a labor intensive effort, and/or requiring specifically designed equipment.

BRIEF SUMMARY OF THE INVENTION

In an embodiment, the present invention relates to a method for observing a change in one or more parameters of a flowable material in a vessel, the method comprising: transmitting an ultrasound signal into a vessel containing a flowable material; observing a change in the ultrasound signal after it has passed through the flowable material; and relating the change in the ultrasound signal to the change in one or more parameters of the flowable material.

In another embodiment, a method for observing a change in one or more parameters of a flowable material in a vessel comprises transmitting an ultrasound signal having a frequency in the range of from about 100 kHz to about 10,000 kHz into a vessel containing a flowable material, the vessel having a transverse diameter in the range of from about 100 mm to about 6000 mm; observing a change in the ultrasound signal after it has passed through the flowable material; and, relating the change in the ultrasound signal to the change in one or more parameters of the flowable material.

In a preferred embodiment, the method includes monitoring the flowable material in the vessel to determine whether agglomerates are present in the flowable material. Alternatively, or additionally, a preferred embodiment of the method includes monitoring fermentation in the vessel.

Embodiments of the invention can be carried out using a variety of vessels, e.g., a "reusable" vessel such as a metal vessel, or a "disposable" vessel such as a plastic vessel.

BRIEF DESCRIPTION OF THE SEVERAL VIEWS OF THE DRAWING(S)

DETAILED DESCRIPTION OF THE INVENTION

Figure 1:
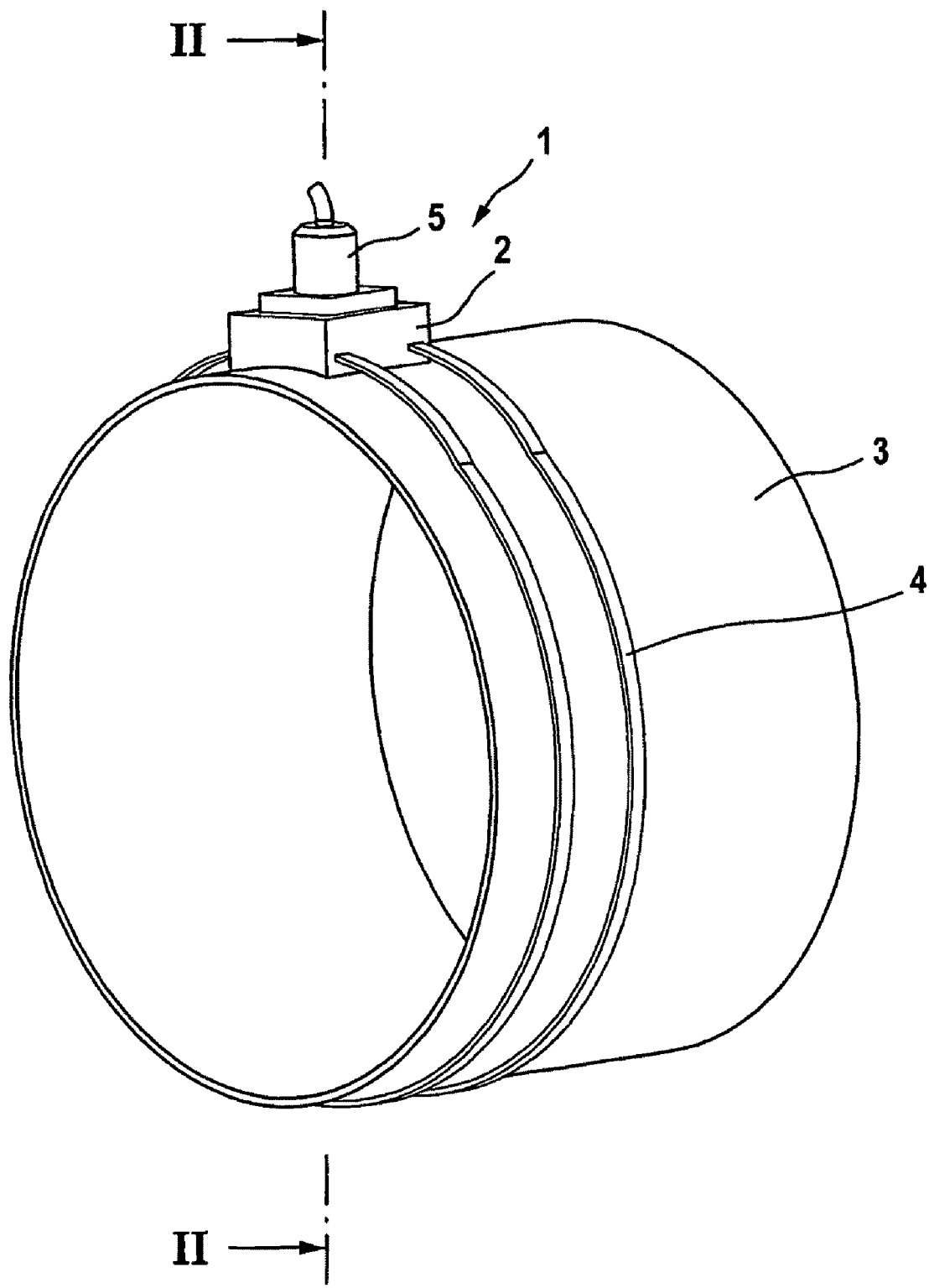
FIG. 1 shows a perspective view of a slice through a vessel with an ultrasound emitter unit attached to it.

In an embodiment, the present invention relates to a method for observing a change in one or more parameters of a flowable material in a vessel, the method comprising: transmitting an ultrasound signal into a vessel containing a flowable material; observing a change in the ultrasound signal after it has passed through the flowable material; and relating the change in the ultrasound signal to the change in one or more parameters of the flowable material.

In another embodiment, a method for observing a change in one or more parameters of a flowable material in a vessel comprises transmitting an ultrasound signal having a frequency in the range of from about 100 kHz to about 10,000 kHz into a vessel containing a flowable material, the vessel having a transverse diameter in the range of from about 10 mm to about 6000 mm; observing a change in the ultrasound signal after it has passed through the flowable material; and, relating the change in the ultrasound signal to the change in one or more parameters of the flowable material.

In some embodiments, the method includes monitoring the change in two or more parameters of the fluid in the vessel.

In an embodiment of the method, the method comprises monitoring one or more of (in some embodiments, monitoring two or more of): appearance of a product, appearance of a target molecule, disappearance of a reactant, increase in the concentration of a contaminant, and decrease in the concentration of a contaminant, in the flowable material in the vessel.

In a more preferred embodiment, the method includes monitoring the flowable material in a vessel to determine whether agglomerates are present. Alternatively, or additionally, another more preferred embodiment of the method includes monitoring fermentation in the vessel.

In some embodiments, the method can be carried out without significantly reducing the presence of bubbles and/or foam in the vessel.

Embodiments of the invention can be carried out using a variety of vessels, e.g., a "reusable" vessel such as a metal vessel, or a "disposable" vessel such as a plastic vessel.

The change in the ultrasound signal after passing through the flowable material may be a change over space, i.e., at different locations in the vessel measured at the same time, a change over time, i.e., at different times but the same location in the vessel, or a mixture of both. Preferably, the change in the ultrasound signal is a change over time recorded at the same location in the vessel.

The change in ultrasound signal may be either a change in the time of flight of the signal through the flowable material, or a change in the amplitude attenuation of the ultrasound signal. Preferably, it is a change in the amplitude attenuation of the ultrasound signal. If the change in ultrasound signal is a change in the time of flight of the signal, adjustments must usually be made to account for the temperature of the flowable material.

The flowable material in the vessel may be a liquid, a gas, a liquid/solid mixture or suspension, a flowable solid, or a mixture of any of these. The fluid can include, for example, one or more of: solutes, particulates, precipitates, flocculates, sols, suspensions, emulsions, micelles, and a mixture of any of these.

The vessel may be, for example, a reaction vessel, such as a fermentor, a bioreactor, or a chemical or pharmaceutical reaction vessel; a storage vessel, e.g., for oil, pharmaceuticals, filtrate, retentate, foodstuffs, water, fuels, fuel gases such as hydrogen or natural gas, chemicals, or fluid waste; a mixing vessel, such as a reacting emulsion as used in making chromatography media; a separation vessel; a crystallisation vessel; or a blood fractionation vessel. The vessel can be made of any suitable material, e.g., metal (for example, stainless steel) or plastic (e.g., a deformable material such as one or more of polypropylene, polyethylene, silicone, an acrylic resin, polyvinyl chloride (PVC), and mixtures thereof, e.g., forming a bag). Typically, in those embodiments wherein the vessel is made of a plastic material, the vessel is a bag, for example, a polyethylene lined bag. A variety of suitable vessels, e.g., for receiving and/or containing a flowable material, are known in the art.

The mode of transmitting an ultrasound signal into the vessel may include attachment of an ultrasound emitter (that can be an ultrasound transceiver) to the outside of the vessel and transmission of an ultrasound signal through a wall of the vessel, inclusion of an ultrasound emitter into a wall of the vessel either in direct contact with or spatially isolated from the flowable material in the vessel, or transmission of an ultrasound signal from an ultrasound emitter via an ultrasound transmissive material through a wall of the vessel. In those embodiments also including the use of a separate ultrasound receiver, the receiver can be attached as described above with respect to the ultrasound emitter.

Preferably, the ultrasound signal is transmitted into the vessel by an ultrasound emitter which is not in direct contact with the flowable material in the vessel. More preferably the ultrasound emitter is attached to the outside of the vessel and transmits the ultrasound signal through a wall of the vessel. Even more preferably, the ultrasound signal is transmitted from the ultrasound emitter to a wall of the vessel by an ultrasound transmissive material there between. In preferred embodiments, the ultrasound emitter (and ultrasound receiver, if present) is removably attached to the outside surface of the vessel.

In a preferred embodiment, the one or more parameters (in some embodiments, the two or more parameters) in the vessel are selected from pressure, solute concentration in a fluid, solid particulate concentration in a flowable material, structural characteristics of solid particulates in a flowable material, e.g., the size and/or morphology of crystals. Embodiments of the invention include observing a process taking place in a flowable material (and thus, monitoring one or more parameters in the processed flowable material), at the measurement location or elsewhere in the vessel, such as fermentation, chemical synthesis, precipitation, aggregation, crystallisation, degradation of foodstuffs, e.g., souring of milk, or contamination of a liquid or liquid/solid mixture.

In the present method the observation of a change in the ultrasound signal after it has passed through the flowable material may be by a separate ultrasound receiver spaced apart from the ultrasound emitter and arranged to receive an ultrasound signal emitted by the ultrasound emitter after the signal has passed through the flowable material. Alternatively, the observation of a change in the ultrasound signal may be by an ultrasound transceiver arranged to receive an ultrasound signal after it has passed through the flowable material.

In an embodiment, an ultrasound transceiver acts as both the ultrasound emitter and the ultrasound receiver. In some embodiments, the ultrasound pulse is emitted from the ultrasound transceiver, is reflected by an ultrasound reflector and is received by the same ultrasound transceiver, the ultrasound signal having passed through the flowable material. In other embodiments, the ultrasound pulse is reflected without using an ultrasound reflector, e.g., a wall of the vessel reflects the pulse.

In another embodiment, the present invention provides an ultrasound emitter unit comprising an ultrasound emitter and a means of attaching the ultrasound emitter to a vessel containing a flowable material.

Furthermore, an apparatus according to an embodiment of the present invention includes an ultrasound measurement vessel comprising a vessel, for containing a flowable material, an ultrasound emitter, and an ultrasound receiver.

In an embodiment of the apparatus, the ultrasound emitter can be an ultrasound transceiver. A variety of ultrasound emitters, transceivers, and receivers are suitable for use in the invention. In one embodiment, a CLAD ultrasonic transceiver, comprising a core and cladding (acting as a collimator), can be used. Such a device, that reduces or eliminates spurious ultrasonic noises, can be especially desirable for use with a disposable plastic (e.g., polyethylene) vessel, wherein the disposable vessel containing flowable material is placed on a rocker or agitator, more preferably, wherein the prove of the device is placed in contact with the vessel near the center of the vessel where there is minimum change in path length. One example of a CLAD transceiver is marketed by Synthesarc, Inc. (Quebec, Canada).

Preferably, the ultrasound emitter unit comprises a mounting block, an ultrasound emitter set in a socket in the mounting block, and means for attaching the mounting block to a vessel. A variety of mounting blocks and means for attaching the mounting blocks are suitable for use in the invention. More preferably, the mounting block has a vessel interface surface with an opening in it to allow an ultrasound signal from the ultrasound emitter to be emitted out of the vessel interface surface without passing through the mounting block. Preferably there is an ultrasound transmission space between the ultrasound emitter and the surface of a vessel when the ultrasound emitter unit is in place on the surface of the vessel.

Preferably, the ultrasound emitter unit also comprises an access hole into the ultrasound transmission space allowing it to be filled with ultrasound transmissive material (couplant) when the ultrasound emitter unit is in place on the surface of a vessel.

The ultrasound transmission space is preferably filled with an ultrasound transmissive material (the couplant), e.g., held in place with, for example, a film, such as a plastic film. This material may be, for example, water, other liquid, or ultrasound transmissive paste or gel. A variety of ultrasound materials are suitable. Preferably the ultrasound transmissive gel is a polyalcohol, e.g., with either ketone or aldehyde substituents. It may be a proprietary product from Pall Euroflow Ltd.

By conforming exactly and filling the interface between the components, the ultrasound transmissive material ensures efficient communication of the ultrasound signal from the ultrasound emitter which is set in the socket, and the surface of the vessel on which the unit is mounted.

In this embodiment, the ultrasound emitter is preferably sealed in the socket by an O-ring seal which is either set into the ultrasound emitter and provides a sealing interface against a smooth wall of the socket, or set into the wall of the socket and provides a sealing interface against a smooth surface of the ultrasound emitter. This O-ring seal prevents any ultrasound transmissive material which is inserted in the ultrasound transmission volume from escaping between the walls of the socket and the ultrasound emitter inserted therein.

Preferably, the vessel interface surface has a seal which seals against the surface of the vessel against which the ultrasound emitter unit is fixed. This seal inhibits the ultrasound transmissive material from escaping from the ultrasound transmission volume where the mounting block meets the vessel. Preferably the seal is formed from a resilient material such as rubber or foam. More preferably this seal forms a watertight seal between the vessel and the mounting block.

In general, the ultrasound emitter unit (and receiving unit, if present) may be attached to various different shapes and sizes of vessel. In one embodiment, where the unit(s) also comprises a resilient seal on the vessel interface surface, the resilient seal deforms to accommodate various surface curvatures and therefore to allow attachment of the unit(s) to many different sizes of vessel.

The means for attaching the mounting block to a vessel may comprise any temporary or permanent means. Temporary means may include, for example, one or more straps, springs, clamps or brackets passing around or through the ultrasound emitter unit and attaching around or to the vessel, magnetic fixing means, screws or bolts passing through the ultrasound emitter unit and attaching to the vessel, or hook and eye fixings. Permanent means may include, for example, adhesive, welding, or soldering.

Typically, embodiments of methods and apparatus according to the invention utilize ultrasound signals with a frequency of between about 100 kHz and 10,000 kHz. More typically, lower frequencies are preferred for use with larger diameter vessels, and higher frequencies are preferred for use with smaller diameter vessels.

For example, in some embodiments wherein the vessel is a re-usable vessel such as a metal (e.g., stainless steel) vessel, having a transverse dimension, e.g., diameter, of greater than about 800 mm, for example, in the range of about 1000 mm to about 6000 mm, e.g., about 1000 mm to about 2000 mm, or about 3000 mm to about 6000 mm, the frequency of the ultrasound signal is typically about 100 kHz to about 10 MHz (10,000 kHz), in some embodiments about 100 kHz to about 500 kHz, and in some other embodiments, about 100 kHz to about 250 kHz. Typically, in those embodiments wherein the metal vessel has a diameter of about 3000 mm to about 6000 mm, the frequency of the ultrasound signal is about 100 kHz to about 500 kHz.

In yet some other embodiments wherein the vessel is a re-usable vessel such as a metal vessel, having a transverse dimension, e.g., diameter, of about 1000 mm or less, e.g., in the range of about 10 mm to about 800 mm, the frequency of the ultrasound signal is typically about 500 kHz to about 10 MHz (10,000 kHz).

In some other embodiments wherein the vessel is a disposable vessel such as a plastic (e.g., polyethylene or polypropylene) vessel, having a transverse dimension, e.g., diameter (during use), of greater than about 800 mm, for example, in the range of about 1000 mm to about 6000 mm, e.g., about 1000 mm to about 2000 mm, or about 3000 mm to about 6000 mm, the frequency of the ultrasound signal is typically about 100 kHz to about 1 MHz (1000 kHz), in some embodiments, about 100 kHz to about 500 kHz.

In yet some other embodiments wherein the vessel is a disposable vessel such as a plastic vessel, having a transverse dimension, e.g., diameter, of about 1000 mm or less, e.g., in the range of about 10 mm to about 1000 mm, the frequency of the ultrasound signal is typically about 500 kHz to about 10 MHz (10,000 kHz).

In yet another embodiment of the method, the frequency of the ultrasound signal is about 100 kHz to about 1 MHz (1000 kHz), e.g., about 100 kHz to about 250 kHz, and the vessel is of a transverse dimension, e.g., diameter, of about 800 mm or greater, preferably up to 10 metres (10000 mm) and maybe greater than 10 metres.

Alternatively, in another embodiment, the frequency of the ultrasound signal is about 250 kHz to about 10 MHz (10,000 kHz), e.g., about 250 kHz to about 10 MHz, and the transverse dimension, e.g., diameter, of the vessel is between 12 mm and 25 mm.

For example, in an embodiment, the present apparatus utilises ultrasound signals with a frequency of between about 100 kHz and about 1 MHz (1000 kHz). The lower frequencies, e.g., 100-250 kHz, are, in some embodiments, preferred for longer path lengths, such as about 800 mm or greater, whereas the higher frequencies, e.g., greater than about 1 MHz, are, in some embodiments, preferred for shorter path lengths, such as 12 mm, 25 mm, or 400 mm. Thus, the preferred ultrasound frequency range varies according to the size of the vessel.

In some embodiments, the lower frequency ultrasound signals are particularly useful for longer path lengths, e.g., greater than 800 mm, for example, in larger diameter vessels. In some embodiments, the higher frequency ultrasound signals, e.g., greater than about 1 MHz, do not show a good response over path lengths greater than about 800 mm. Frequencies between 100 and 500 kHz, in some embodiments, between 100 and 250 kHz, are particularly useful for steel vessels greater than about 800 mm in diameter.

In accordance with embodiments of methods according to the invention, amplitude attenuation of the ultrasound signal is defined as the difference between the amplitude of the signal emitted from the ultrasound emitter and the amplitude of the ultrasound signal received by the ultrasound receiver after having passed through the flowable material in the vessel. In some embodiments of the methods and apparatus of the invention, the ultrasound emitter and receiver are combined in an ultrasound transceiver. In one embodiment, the ultrasound signal is emitted from the transceiver, passes through the flowable material, is reflected by an ultrasound reflector, which may be the opposite side of the vessel, and is received by the ultrasound transceiver. In other embodiments, the ultrasound signal is reflected without an ultrasound reflector (e.g., reflected by a plastic wall of the vessel), or an ultrasound receiver receives the signal.

Furthermore, it is possible to place a number of ultrasound emitter units (and optional ultrasound receiver units) on the outside of a single vessel. This allows measurement of the parameters of a flowable material in the vessel at a number of different locations in the same vessel.

In the methods and apparatus described, the generation of the ultrasound signal, to be passed through the flowable material in the vessel, is controlled by signal generation apparatus connected to the ultrasound emitter. This signal generation apparatus may control such parameters as the duration of each pulse, the frequency of occurrence of the pulses, the power of each pulse, and parameters which depend on the size and shape of vessel through which the ultrasound signal is passed and the frequency of the ultrasound.

The ultrasound signal which has passed through the flowable material in the vessel is analysed by signal processing apparatus, for example, standard signal processing apparatus. This signal processing apparatus may include controls to select one or more of: the range of frequencies being observed, the gain of signal amplifiers, preferences for recording of the signal over time, and preferences for the displaying the received signal on various output devices, alarm signals, and recording of the received signal, e.g., tracking the production of a product such as a pharmaceutical, to data logging apparatus, e.g., in accordance with one or more of the following (in some embodiments, two or more of the following): 21 CFR 11, cGAMP, GxP-related systems (e.g., Good Laboratory Practice (GLP), Good Clinical Practice (GCP), and/or Good Manufacturing Practice (GMP)), Rapid Microbiological Methods, and carrying out process validation, e.g., in accordance with Process Analytical Technology (PAT).

The signal processing apparatus may be operated remotely via, for example, RS232, USB, GPIB, and/or Ethernet connection(s).

The methods and apparatus described may be used particularly to measure, more preferably monitor, changes in concentration of components of a flowable material in a vessel. This may include monitoring one or more of (in some embodiments monitoring two or more of): the appearance of products, target molecules, the disappearance of reactants, the increase or decrease in the concentration of contaminants and/or desired products in the flowable material, the fitness-for-use or efficacy of a product, and a control path that will cause an alarm if the ultrasound "fingerprint" of the reaction or process is outside its normal limits (pathway).

The methods and apparatus described may also provide a negative or positive feedback mechanism wherein the ultrasound trace is monitored by a computer which has a control path with limits which when exceeded act to bring the flowable material in the vessel back within the set limits, e.g., by opening a valve or other such device to provide one or more of: adding a reagent, adding a diluent (e.g., water), adding a buffer/acid/alkali to change the pH, and altering the temperature and/or pressure of a reaction, to bring a process back under control.

Furthermore, these methods and apparatus may also be used to detect changes in the amount of solid material in a flowable material, i.e., the liquid/solid ratio. The described methods and apparatus may also be used to monitor changes in pressure of a flowable material in a vessel. As gases are significantly more compressible than liquids, this application is especially useful for monitoring gases in a vessel.

Embodiments of the present invention may find applications in a wide variety of technical fields. Illustrative examples of such applications are one or more of the following:

(a) monitoring of fermentation, concentration of components or contaminants and/or pressure of flowable foodstuffs, such as milk, wine, or beer, in a vessel. Also, the present invention may be used to indicate if flowable foodstuffs in vessels have degraded, e.g., milk has soured;

(b) measurement of changes in concentration of components or contaminants and/or pressure of crude or other oils in oil vessels;

(c) monitoring of changes in the concentrations of components or contaminants and/or pressure of, for example, synthetic or biosynthetic chemicals, pharmaceuticals or neutraceuticals in vessels before, during and/or after synthesis, for example, by fermentation processes, or continuous or batch reactor processes;

(d) monitoring of changes in concentration of contaminants and/or pressure of water, such as potable water or effluent, in vessels, or measurement of changes in amounts of suspended solids in waste or potable water in vessels;

(e) monitoring of changes in concentration and/or pressure of hydrocarbons or hydrogen in vessels in hydrogen generation apparatus;

(f) monitoring of changes in concentrations of components and/or pressure of dialysis fluids, such as hemofiltrates, in vessels;

(g) monitoring of changes in concentration of components or contaminants and/or pressure of any gases, such as natural gas, in vessels;

(h) monitoring of changes in phase behaviour in two-phase synthesis reactions, such as formation of polymethacrylate or styrene-divinylbenzene (DVB), e.g., forming beads for chromatography;

(i) monitoring of changes in the physical parameters, such as size and/or morphology, of components or contaminants in the flowable material, e.g., the formation and/or presence of agglomerates in the flowable material, e.g., agglomerates of proteins such as antibodies in the vessel, crystals in suspension (e.g., insulin) in a vessel;

(j) monitoring of precipitation reactions or changes in flowable suspensions in vessels;

(k) monitoring of changes in physical parameters of a fluidised bed in a vessel;

(l) monitoring of changes in the physical parameters of expanded bed filtration or capture systems. These parameters may include detection of when the system reaches the stable expanded bed condition, and/or the monitoring of the capture step of the expanded bed filtration process;

(m) monitoring of changes in physical parameters of fermentation reactions in vessels, such as production of alcohol (beer, wine, etc.) and some foodstuffs, for example, soya.

Thus, the vessel may be a reactor or fermentor, or a storage or transportation vessel. Typically, it is other than a packed-bed chromatography column.

Applications (c), (i), (l) and (m) from the list above are particularly preferred. Additionally, or alternatively, embodiments of the invention are particularly suitable for process validation, e.g., Process Analytical Technology (PAT).

In more preferred embodiments, applications including monitoring two or more parameters via two or more emitters can be desirable so that processing conditions can be adjusted to allow one or more parameters to reach a set limit, predetermined value, or range of values. For example, if the change in concentration of one or more components reaches an undesirable value, one or more other monitored parameters (e.g., monitored at a different location and/or at a different frequency) can be adjusted to allow the concentration of one or more components to reach or return to a desirable (e.g., predetermined) value or range of values. Alternatively, or additionally, one or more parameters can be monitored via ultrasound, and one or more other parameters and/or aspects (e.g., one or more of pH, nutrient feed, aeration, and agitation rate) can be monitored without using ultrasound, so that processing conditions can be adjusted to allow one or more parameters to reach a set limit, predetermined value, or range of values.

The following are some additional examples of applications in accordance with embodiments of the invention:

In fermentation or cell culture (e.g., in suspension, in perfusion, or in cell attached system) producing, for example, one or more of antibodies (e.g., monoclonal antibodies), proteins, peptides, recombinant proteins, plasmids, and viruses, ultrasound can be used to measure, e.g., monitor, one or more of the following in vessels: state of cells in suspension (agitation), cell growth rate, and product (e.g., protein) expression level. As noted above, in more preferred embodiments, monitoring two or more parameters can be desirable so that processing conditions can be adjusted to allow one or more parameters to reach a predetermined value or range of values.

In accordance with embodiments of the invention, ultrasound can be utilized at a variety of points in a system including processing the flowable material in a vessel. For example, as part of a purification and/or separation process, e.g., including centrifugation, filtration and/or chromatography, and/or at other points in processing, the process fluid may pass into a holding tank or chaperone tank, where ultrasound can be used to measure, preferably monitor (including characterizing), the process fluid in the vessel.

Alternatively, or additionally, as part of, for example, producing a biopharmaceutical, a target molecule, e.g., a protein, nucleic acid or compound, in a vessel such as a holding tank or chaperone tank, one or more of the following can occur: purification, concentration, dimerization, oligomerization, polymerization, crystallization, oxidation, hydrolysation, denaturation, primary, secondary, tertiary and quaternary structure formation. Furthermore the target molecule in the vessel, can, for example, agglutinate, be placed in contact with a refolding catalyst, denature, and/or become contaminated. In accordance with embodiments of the invention, one or more of these aspects can be measured, preferably monitored, by ultrasound.

After one or more of centrifugation, filtration (including, but not limited to, one or more of dead-end filtration, cross-flow filtration, diafiltration, sterile filtration, microfiltration and ultrafiltration) and chromatography (e.g., fluidized bed, expanded bed, adsorption, absorption), ultrasound can be used to confirm and/or control one or more of removal efficiency of unwanted contaminants (such as cells and cell debris) and the transmission level of the desired product(s). In some applications, the quick results obtained from utilizing ultrasound allow the processing system to be quickly optimized to provide increased cell concentration while reducing dilution and/or cell damage/product loss.

With respect to applications including filtration, in some embodiments of the invention, ultrasound can be used to measure, e.g., monitor and/or control, the presence or absence of filtrate/permeate product in the receiving vessel (e.g., a holding tank). With respect to applications including cross-flow filtration and/or diafiltration, in some embodiments of the invention, ultrasound can be used to measure, e.g., monitor and/or control, the concentration of retentate product and/or to measure, e.g., monitor and/or control, the presence or absence of filtrate/permeate product in the receiving vessel (s).

In all of the above applications, a series of ultrasound emitter units (and, optionally, a series of ultrasound receiver units) may be used instead of only a single unit. This means that the properties of the flowable material inside the vessel may be measured at different points along the vessel.

Using such an array of ultrasound units, it is possible to measure, preferably, monitor, changes in parameters and the propagation of these changes through a vessel. For example, when a flowable material having a high concentration of solute is diluted in a vessel, it is possible to monitor the diffusion of the solute through the flowable material in the vessel, along with the concentration of the solute after dilution. Alternatively, for example, agglutination or dimerization, oligomerization and/or polymerization, e.g., the formation of agglomerates in the flowable material, can be measured, e.g., detected and/or monitored, e.g., the formation of agglomerates increases attenuation, and causes the signal to drop. The start of agglomeration will cause noise, and thus the signal-to-noise (S/N) ratio will get smaller. As further agglomeration occurs, the S/N ratio will get lower. Thus, a drop in the S/N ratio (e.g., an increase in noise), suggests agglomeration. A further decrease in the S/N ratio (e.g., a further increase in noise) suggests more agglomeration. Ultrasound can be used to monitor, for example, in addition to the change in the S/N ratio, the viscosity increase (e.g., the concentration of agglomerates is proportional to the attenuation of the ultrasound) and/or the pressure increase associated with agglomeration.

In all of the above listed applications the changes may be observed over time, e.g., observed empirically over time. Embodiments of the invention may be used to measure, e.g., monitor, parameters in vessels in real time and to indicate when changes occur in the flowable material in the vessel. By comparison of the ultrasound signal recorded from a given vessel with previous signals recorded when certain features of the flowable material were changed, e.g., when milk soured or when a chemical product being formed by a reaction in a vessel was impure, these changes can be detected in real time when they occur again. This is especially useful for monitoring of a flowable material in a vessel for quality control purposes. As well as monitoring the quality of a fluid product, embodiments of the methods and apparatus of the present invention are useful for monitoring the progress of a process. In this situation, the ultrasound response can be used to indicate, for example, when a process has reached completion, or has reached a certain stage. Embodiments of the invention are especially suitable for one or more of PAT, cGAMP, GxP-related analysis, and RMM.

As well as monitoring the quality of a flowable material, embodiments of the present invention are useful for monitoring the progress of a process in a vessel. In this situation, the ultrasound response of the flowable material can be used to indicate, for example, when a process has reached completion, or has reached a certain stage. For example, monitoring a reaction by comparison of the ultrasound attenuation trace with the trace recorded during previous (e.g., successful) reactions.

Embodiments of the invention will now be described in detail, by way of example, with reference to the accompanying illustrative figures.

The embodiment illustrated in FIG. 1 shows an ultrasound emitter unit 1 attached to a vessel 3. A mounting block 2 is attached to the vessel 3 by straps 4 passing through the mounting block 2 and around the vessel 3. As the mounting block 2 is not attached to the vessel 3 in any other way, it can easily be detached from the vessel 3 or moved into another position, or maybe onto another vessel. Furthermore, the straps 4 are adjustable and allow the ultrasound emitter unit to be attached to vessels of different sizes.

FIG. 1 shows the mounting block 2 with the ultrasound emitter 5 in place in a socket in the mounting block.

Figure 2:
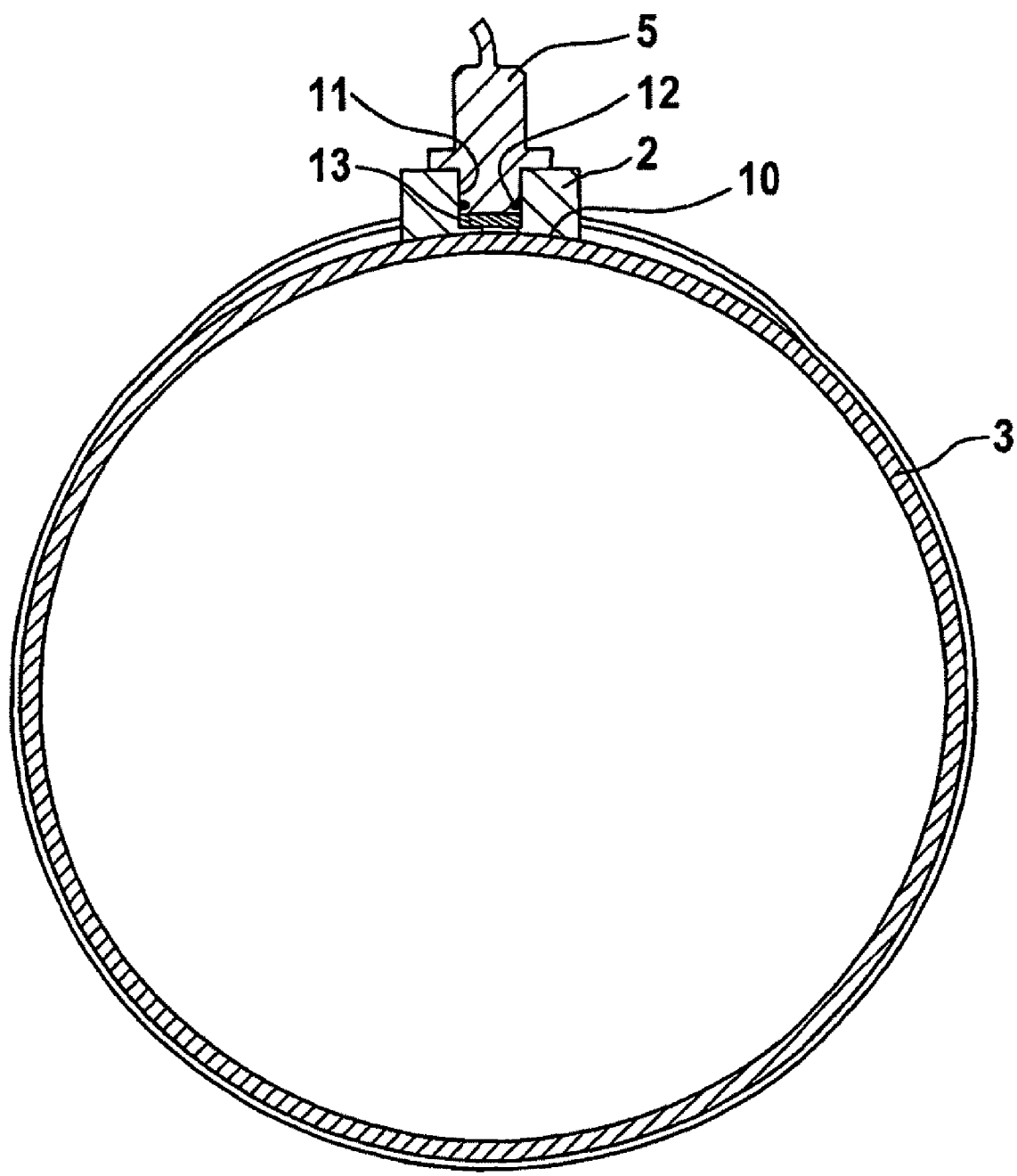
FIG. 2 shows a cross section, along II-II of FIG. 1, of a slice through a vessel with an ultrasound emitter unit attached to it.

FIG. 2 shows a cross-section along 11-11 in FIG. 1. The mounting block 2 has a vessel interface surface 10 with a seal on it to provide a seal against the surface of the vessel 3. The mounting block 2 has an ultrasound emitter 5 in the socket 11. The ultrasound emitter 5 has a recess holding an O-ring 12 in the part which protrudes into the mounting block 2. This O-ring 12 provides a seal between the ultrasound emitter 5 and the mounting block 2.

An ultrasound transmissive gel 13 (couplant) is placed between the ultrasound emitter 5 and the surface of the vessel 3 against which the mounting block 2 is attached. This material ensures a good transmission of the ultrasound signal between the ultrasound emitter 5 and the surface of the vessel 3.

Figure 3:
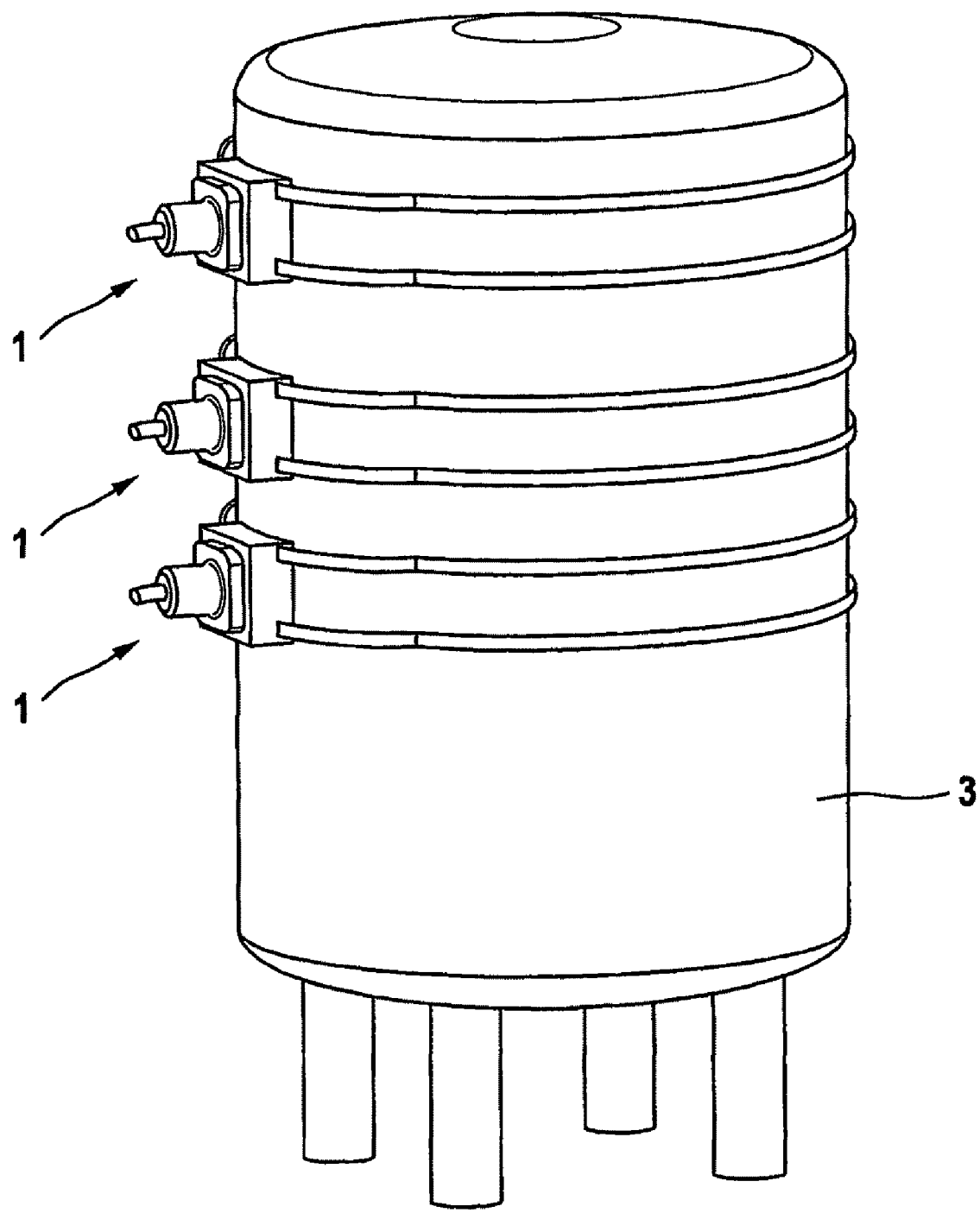
FIG. 3 shows a vessel having three ultrasound emitters attached to the outside of it.

FIG. 3 shows a vessel 3 with a series of three ultrasound emitter units 1 strapped against the outer wall of the vessel 3 at different positions up the side of the vessel. This allows measurements of the parameters of the flowable material inside the vessel to be taken at different points in the vessel.

The following examples further illustrate the invention but, of course, should not be construed as in any way limiting its scope.

Example 1

A simple yeast and sugar fermentation bio-reaction was conducted in a 400 mm diameter reaction vessel. Prior to the fermentation, the inside of the reaction vessel and all nozzles, tubing and pump were sterilized with VWP Sterilizer (B & J Home brew, Stroud, Glos., UK) for 10 minutes.

8 kg of sucrose was added to 21 liters of hot water (80° C.) in the reaction vessel yielding 25 liters of solution. This reaction solution was allowed to cool overnight. To this mixture was added a sachet of Alcotec 48 Turbo Super Yeast powder (B & J Home brew, Stroud, Glos.) a proprietary yeast nutrient mixture that provides all the nutrients and yeast to ferment 8 kg of sucrose in 25 liters of water. A space heater was placed adjacent to the reaction vessel to increase the surrounding air temperature to approximately 24° C.

The progress of the reaction was observed by an array of ultrasound transducers distributed up the outside wall of the vessel. No air trap was fitted to the reaction vessel as the fermentation was too rapid to allow the slow release of $CO_2$. Thus, only a wrap over lid was positioned on top of the reaction vessel.

Ultrasound readings were recorded every 10 minutes for over 8 days and then plotted over the time in hours.

The specific gravity of the reaction mixture was measured at the start of the experiment and throughout the fermentation along with the ultrasound readings.

The fermentation was allowed to progress to completion, at which point the yeast cells expired and sedimented out of solution, resulting in natural clearing of the broth.

The array of sixteen 1 MHz (1000 kHz) ultrasound transducers was attached to the vertical wall of the reaction vessel. The bottom nine transducers were below the surface level of the liquid with the tenth transducer from the bottom being at the interface between the reaction liquid and the atmosphere above the reaction liquid.

Ultrasound pulses were projected across the reaction vessel by applying voltage to the piezo-electric crystal transceivers. A detector was used to monitor any reflected ultrasound signal on the crystal. The detector gave a readout as the change in amplitude of the reflected sound pulse. An automatic gain control (AGC) is used to change the gain to make the trace on the screen and on the output 80% full screen. Thus, the y-axis is that gain required to return the output signal to 80% maximum output, the x-axis is time. Accordingly, the bigger the signal, the more the ultrasound is attenuated.

At approximately 8 hour intervals the specific gravity of the broth was measured. This parameter was used to follow directly the conversion of sucrose to ethanol by the yeast. The ultrasound values are found to follow directly the specific gravity information once the fermentation had passed a particular point. The end point of the fermentation, i.e., when the specific gravity parameter fell to a constant level, was in correlation, to within about one hour, with the return of the ultrasound amplitude attenuation data to approximately the same level as before the fermentation.

Figure 4:
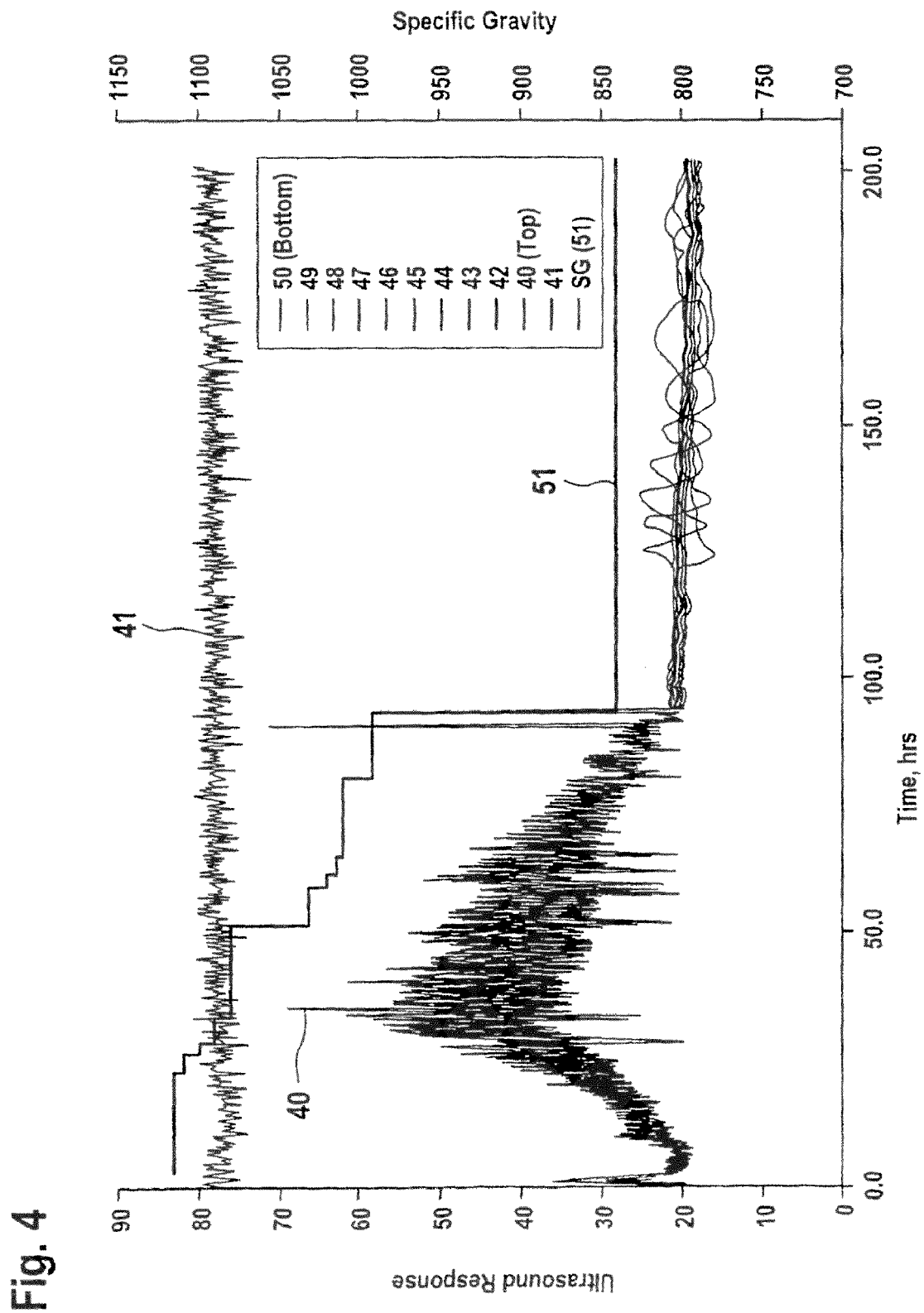
FIG. 4 shows the variation of specific gravity and ultrasound signal amplitude attenuation over time at 11 different locations in a fermentation vessel during a water/glucose solution fermentation process.

FIG. 4 shows the variation over time of the amplitude attenuation of the bottom 10 ultrasound transceivers (i.e., those attached to the reaction vessel at or below the level of the top surface of the reaction mixture). The transducer the trace of which is labelled 40 was half in line with the top of the broth and half in line with the supernatant air, hence its higher attenuation.

Transducer signal 41 (the noisy trace with an ultrasound attenuation between 70 and 80, wherein the transducer was located above the surface layer of the broth) was obtained by passing signals only through the air space above the reaction mixture. This acts as a control signal indicating that the change in ultrasounds response shown by transducers 42 to 50 is a result of the fermentation of the reaction mixture and not simply an artefact of the apparatus.

The specific gravity 51 of the mixture is also shown in FIG. 4.

A number of the sharp spikes in the ultrasound response traces were due to stiring of the reaction mixture.

Figure 5:
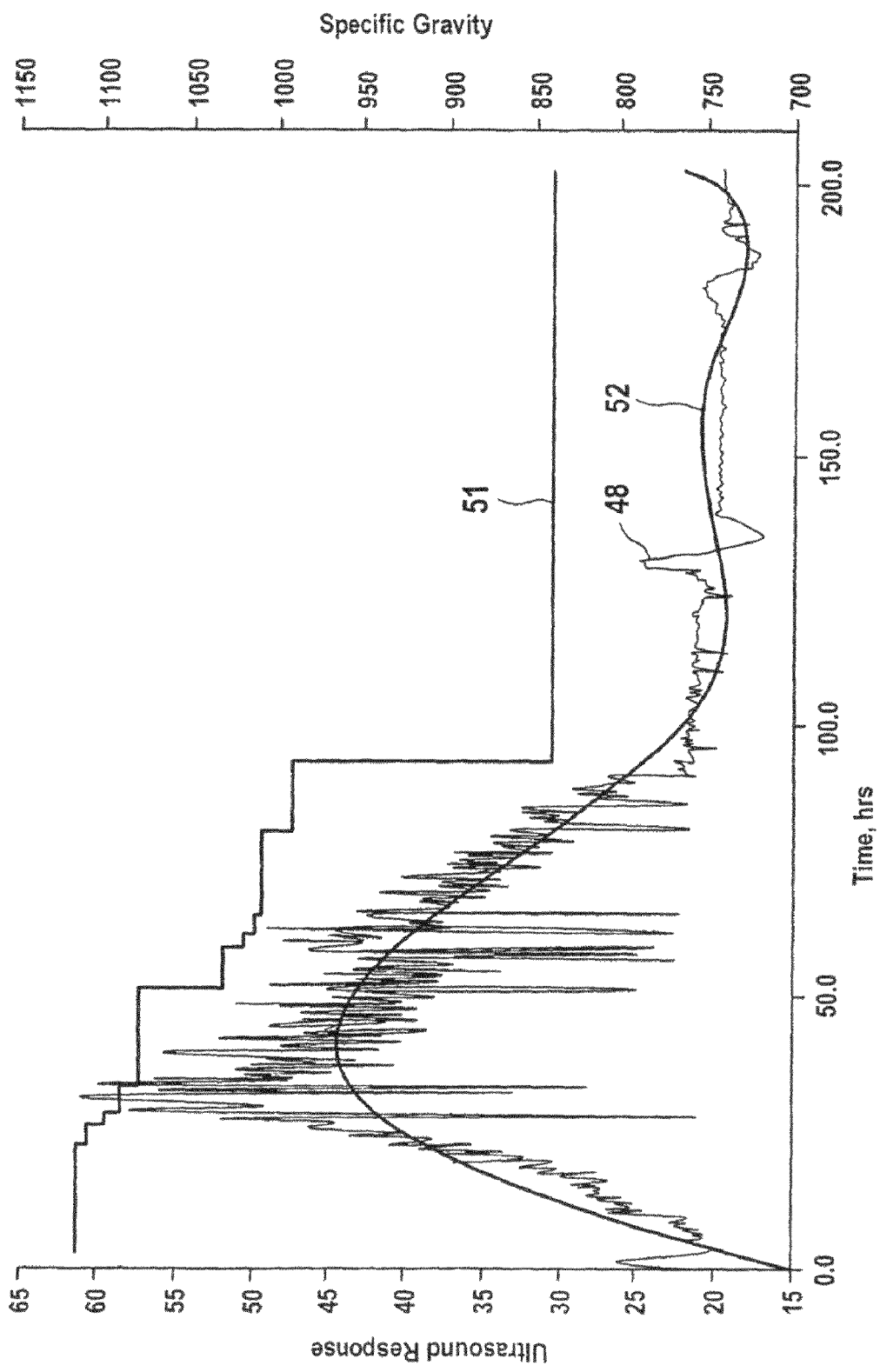
FIG. 5 shows the variation of specific gravity and ultrasound signal amplitude attenuation over time in a water/glucose solution during a fermentation process.

FIG. 5 shows the amplitude attenuation change over time of ultrasound transducer 48 from FIG. 4 (i.e., one of the transducers attached to the reaction vessel below the level of the top surface of the reaction mixture). A polynomial fit 52 to the amplitude attenuation signal 48 is also shown. The specific gravity 51 of the mixture is also shown in FIG. 5.

In FIG. 5, the time at which the fermentation stopped is clearly visible by the stabilisation of the specific gravity reading (when the specific gravity stops changing, this indicates that the conversion of sugar into alcohol has ceased). FIG. 5 also shows that the ultrasound amplitude attenuation returns to around its original value, from the start of the experiment, at approximately the same time as the specific gravity measurements indicate that the fermentation has finished, i.e., about 95 hours into the experiment.

The ultrasound responses from all of the transducers in FIGS. 4 and 5 follows the same general shape of curve indicating that the amplitude attenuation change is following a change in a general parameter of the entire reaction mixture and not a localised parameter change.

A correlation can be seen between the progress of the fermentation as traditionally measured by specific gravity and the ultrasound amplitude attenuation.

This demonstrates the ability of ultrasound to observe the progress of a process in a vessel, in the context of a use to indicate when a fermentation process reaches completion.

In addition, it is possible to use the ultrasound to monitor a fermentation reaction and to compare this with ultrasound traces from previous successful fermentations to show any differences or, possibly more importantly, to indicate that the fermentation has progressed in the same way as a previous successful fermentation (i.e., as a quality control technique).

It can also be seen that after an initial rise, the amplitude attenuation trace decreases with the decrease in specific gravity towards the stable readings when the fermentation is complete.

An ethanol solution attenuates the ultrasound signal to a different extent to the initial sugar solution. Therefore, as the sugar concentration drops and the ethanol concentration rises as fermentation progresses, their effects on the signal attenuation combine—this results in the initial rise in the ultrasound attenuation shown in FIGS. 4 and 5. At the peak of the ultrasound trace in FIGS. 4 and 5, the effect of the sugar concentration on the ultrasound signal is equal to the effect of the ethanol concentration. Then as the ethanol concentration takes over and the sugar concentration decreases the ultrasound attenuation trace falls. Hence the typical repeatable graph shape shown in FIGS. 4 and 5 is produced. If the ultrasound trace varies significantly from that produced by a successful fermentation, once learnt by repetition of good batches, this indicates that the fermentation is going wrong and action is required.

This indicates another use for ultrasound in not only indicating the end of a process but also in tracking its progress over time.

It was noted that the reaction mixture effervesced vigorously during the fermentation process and it was surprising that ultrasound could be used to observe changes in a system with so many bubbles which may act as reflectors or refractors for an ultrasound signal.

Example 2

A wine fermentation reaction was conducted in a 400 mm diameter acrylic reaction vessel and was monitored by an array of ultrasound transducers. Prior to the use, the inside of the reaction vessel and all nozzles, tubing and the pump were sterilized with VWP Sterilizer (B & J Home brew, Stroud, Glos., UK) for 10 minutes. The reaction vessel was fitted with a bubble trap to allow for the release of gas products without admitting air.

A rapid fermentation wine kit was mixed and pumped into the reaction vessel. The kit used in the fermentation was a "Cantina 5 Day Wine Kit" (B & J Home brew, Stroud, Glos., UK) which included "concentrated grape juices", a "Wine Yeast/Nutrient" sachet, a "stabiliser" sachet and two packages of "finings", labelled A and B.

Warm water (30° C.) was added to the grape juice to create a total volume of 21 liters. The wine yeast and yeast nutrient sachet was added and mixed well. This solution was then pumped into the reaction vessel via a bottom nozzle using a pump. An air lock was fitted on to the top of the reaction vessel.

The ambient temperature was kept constant at approximately 24° C. using an electric space heater placed directly beside the reaction vessel. The fermentation was allowed to progress to completion, i.e., the point at which the yeast cells expire and sediment out of solution, resulting in natural clearing of the wine.

The array of sixteen 1 MHz (1000 kHz) ultrasound transducers was attached up the vertical wall of the reaction vessel as in the previous example. The bottom seven ultrasound transducers 61-67 were below the surface level of the reaction liquid. Upon applying a voltage to the piezo-electric crystal transceivers, ultrasound pulses were projected across the column.

A detector was used to monitor any reflected ultrasound signal. The detector gave a readout as the change in amplitude of the reflected sound pulse. These data were displayed in a curve showing that the composition and fermentation progress of the broth could be monitored by ultrasound.

Ultrasound readings were recorded every 10 minutes for over 5 days and then plotted over the time in hours.

Figure 6:
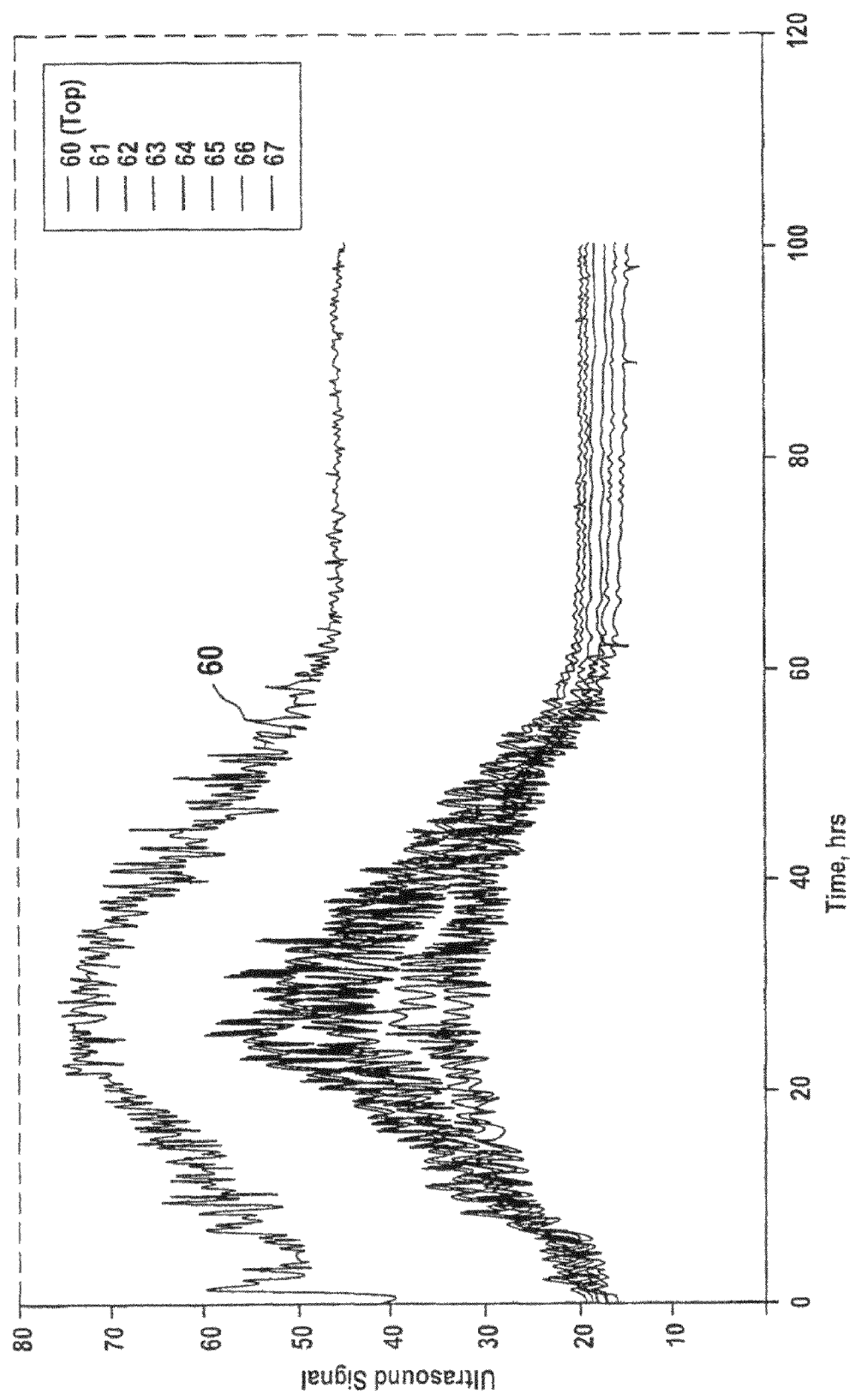
FIG. 6 shows the variation in ultrasound amplitude attenuation over time in a wine fermentation process at eight different locations in the fermentation vessel.

FIG. 6 shows the change in ultrasound amplitude attenuation throughout the fermentation. Note: The ultrasound transducer number 60, at the top of the reaction mixture, was half in line with the top of the reaction mixture and half in line with the supernatant air, hence its higher attenuation.

FIG. 6 indicates that the ultrasound method can be used to observe a fermentation process in a reaction mixture comprising numerous constituents.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for monitoring fermentation in a vessel having a closed end, the method comprising:
   transmitting an ultrasound signal having a frequency in the range of from about 100 kHz to about 1000 kHz through a wall of a vessel comprising a plastic bag, wherein the vessel contains a flowable material;
   observing a change in the ultrasound signal after it has passed through the flowable material;
   relating the change in the ultrasound signal to progress of fermentation in the vessel containing the flowable material; and, purifying a desired fermentation product produced in the vessel.

2. The method of claim 1, including transmitting ultrasound signals from two or more ultrasound emitters through the wall of the vessel into the vessel.

3. The method of claim 1, comprising monitoring fermentation without significantly reducing the presence of bubbles and/or foam in the flowable material in the vessel.

4. The method of claim 1, including transmitting ultrasound signals from two or more ultrasound emitters through the wall of the plastic vessel into the vessel.

5. The method of claim 1, further comprising monitoring the pH in the flowable material.

6. The method of claim 5, including adjusting the pH to reach a range of values.

7. A method for monitoring fermentation in a vessel having a closed end, the method comprising:
- transmitting an ultrasound signal having a frequency in the range of from about 100 kHz to about 1000 kHz through a wall of a metal vessel, wherein the metal vessel contains a flowable material;
- observing a change in the ultrasound signal after it has passed through the flowable material;
- relating the change in the ultrasound signal to progress of fermentation in the metal vessel containing the flowable material; and,
- purifying a desired fermentation product produced in the metal vessel.

8. The method of claim 7, including transmitting ultrasound signals from two or more ultrasound emitters through the wall of the metal vessel into the vessel.

9. A method for monitoring fermentation in a vessel having a closed end, the method comprising:
- transmitting an ultrasound signal having a frequency in the range of from about 100 kHz to about 1000 kHz through a wall of a plastic vessel, wherein the plastic vessel contains a flowable material;
- observing a change in the ultrasound signal after it has passed through the flowable material;
- relating the change in the ultrasound signal to progress of fermentation in the plastic vessel containing the flowable material; and,
- purifying a desired fermentation product produced in the plastic vessel.

10. The method of claim 9, including transmitting ultrasound signals from two or more ultrasound emitters through the wall of the plastic vessel into the vessel.

* * * * *